United States Patent
Been

(10) Patent No.: US 6,626,672 B1
(45) Date of Patent: Sep. 30, 2003

(54) DENTAL PROSTHESIS AND METHOD

(76) Inventor: Larry C. Been, 10246 Midway Rd., Dallas, TX (US) 75229

(*) Notice: Subject to any disclaimer, the term of this patent is extended or adjusted under 35 U.S.C. 154(b) by 57 days.

(21) Appl. No.: 09/607,357

(22) Filed: Jun. 30, 2000

(51) Int. Cl.⁷ .................................................. A61C 5/08
(52) U.S. Cl. ........................ 433/223; 433/207; 75/955
(58) Field of Search ................................ 433/207, 223, 433/228.1; 420/510, 511; 75/955

(56) References Cited

U.S. PATENT DOCUMENTS

| | | | |
|---|---|---|---|
| 145,982 A | 12/1873 | Blake et al. | |
| 1,169,753 A | 1/1916 | Peschko et al. | |
| 1,449,154 A | 3/1923 | David et al. | |
| 1,680,598 A | 8/1928 | Dreaper et al. | |
| 3,585,064 A | * 6/1971 | Prosen | 427/374.2 |
| 4,201,577 A | * 5/1980 | Ingersoll et al. | |
| 4,273,580 A | * 6/1981 | Shoher et al. | |
| 4,326,889 A | * 4/1982 | Sperner | 106/35 |
| 4,426,404 A | * 1/1984 | Shoher et al. | 433/223 |
| 4,427,501 A | * 1/1984 | Rogers | |
| 4,434,211 A | * 2/1984 | Shoher et al. | |
| 4,676,751 A | * 6/1987 | Shoher et al. | 433/222 |
| 4,814,008 A | 3/1989 | Shoher et al. | |
| 4,838,790 A | * 6/1989 | Koller | 433/219 |
| 5,238,751 A | * 8/1993 | Van Der Zel | |
| 5,336,091 A | * 8/1994 | Shoher et al. | 433/215 |
| 5,593,305 A | * 1/1997 | Shoher et al. | 433/218 |
| 5,730,600 A | * 3/1998 | Shoher et al. | 433/223 |

OTHER PUBLICATIONS

Gramm GmbH, Gramm Technik Dental Electroforming Techniques, 1999.

Ross W. Nash, D.D.S., "An Esthetic Alternative to Conventional Porcelain–Fused–to–Metal Crowns," Chairside, Dec., 1997, pp. 1160–1163.

Itzhak Shoher and Aharon Whiteman, "Captek–A New Capillary Casting Technology for Ceramometal Restorations," New Technology, 1995, pp. 9–20.

Itzhak Shoher and Aharon Whiteman, Captek Manual, 1994.

Grant P. Day and Rosemary Devlin, "Flexobond: A Direct Adaptation Technique for Metal Substructures," Sep., 1986, pp. 21–26.

Carl H. Rousseau, "A Simple and Effective Technique," Jan.–Feb. 1985, pp. 57–64.

Melvin A. Engelman, DDS, Victor Zamaloff, CDT and Lori Daena Cooke, CDA, "Ringless Casting with Noble or Base Metal Alloys for Greater Simplicity, Economy and Productivity," Nov., 1985, pp. 12–16.

Milton Solomon, "Surface Roughness and Procelain Bond," Materials and Material Science, Oct., 1980, pp. 65–70.

J.M. Ney Company, "Bridge & Inlay Manual", 1964, pp. 27, 119, 123.

Dr. Niwut Juntavee, Dr. Dan Nathanson and Dr. Russell Giordano "A Research Report on Captek.".

* cited by examiner

Primary Examiner—Ralph A. Lewis
(74) Attorney, Agent, or Firm—Gardere Wynne Sewell LLP; Kenneth T. Emanuelson

(57) ABSTRACT

An alloy and method is disclosed for forming an improved dental prosthesis. The invention relates to a dental material of a precious metal composition and a method for infiltrating one alloy with another to produce a substructure for ceramic prosthetic restorations for damaged or missing teeth or metal replacements for same.

9 Claims, 3 Drawing Sheets

DENTAL PROSTHESIS AND METHOD

FIELD OF THE INVENTION

This invention relates to dental prosthetics, and more specifically to a dental prosthesis and a method for forming a dental prosthesis.

BACKGROUND OF THE INVENTION

Damaged teeth are commonly restored using a crown or inlay. Similarly, missing teeth are commonly restored using a bridge. These crowns, inlays or bridges may be comprised of metal, ceramic, acrylic, composite or a combination of these materials. In addition, these crowns, inlays or bridges are typically formed using an investment, or "lost wax" process.

The investment process begins with the formation of an impression of the pontic area, which has been prepared by a dentist to receive the crown, inlay or bridge. A model and die, which duplicate the shape of the patient's teeth and gums, are then formed from this impression using a plaster type material. A pattern is then formed over this die, thus producing a likeness of the crown, inlay or bridge to be created. The pattern is generally made of an organic material, such as wax.

The pattern is invested in (i.e. coated with) a gypsum type material having a high dimensional stability and resistance to elevated temperatures. The pattern and gypsum investment are then subjected to temperatures sufficient to melt or vaporize the pattern so that the pattern material exits the gypsum structure, leaving a cavity inside the gypsum investment corresponding to the shape of the pattern. The cavity within the investment is then filled with the restorative material of choice, thus creating a reproduction of the pattern in the chosen material (metal, ceramic, acrylic, composite, etc.).

When a crown, inlay or bridge is to have a ceramic layer, a substructure is first constructed to reinforce and accept the ceramic layer. These substructures are generally comprised, in whole or in part, of metallic alloys. Problems have occurred in the use of such alloys due to the fact that the alloys generally contain trace elements that produce oxides on the surface of the alloys. These oxides are sometimes visible through the ceramic layer, making it difficult to produce ceramic restorations having a natural appearance. In addition, some of these oxides are known to have a toxic effect on the surrounding tissue. Although some techniques have been developed to address these problems by using a sintering process, these techniques are both costly and extremely sensitive to process parameters. Accordingly, there is a need for a dental prosthesis and a method of forming a dental prosthesis that is inexpensive and tolerant to variations in the process parameter.

BRIEF SUMMARY OF THE INVENTION

An improved dental prosthesis has been developed comprising a metal alloy for use with the lost wax technique in conjunction with an infiltration process. This material may be used to produce inlays, crowns, bridges and substructures for ceramic restorations having significantly improved aesthetics and overall performance over previously known methods.

One group of embodiments of the present invention comprise dental prosthetic structures comprising a substructure comprising a casting alloy of a first precious metal and a second precious metal, and a coating that permeates the surface of the substructure, the coating comprising an infiltration alloy comprising the first precious metal.

The casting alloy is melted and cast into shape by a suitable method such as investment casting, and the infiltration alloy is then applied to the surface of the substructure and combined with the substructure through a heat treatment process. It is desirable that the cast alloy be both resistant to oxidation and compatible with the surrounding living tissue. In certain embodiments, gold is the major element of the cast alloy due to its characteristics of workability, resistance to oxidation and color, especially useful with ceramics.

In certain embodiments, the casting alloy is comprised of only two elements, gold and platinum. In certain embodiments,:the ratio of platinum to gold in the casting alloy is from 0 to 20% by volume. The percentage of each element is variable, and may be modified for different requirements as to the strength and melting temperature of the alloy for particular applications. The use of a higher ratio of platinum to gold has been shown to increase the strength of the alloy. In one embodiment, the melting temperature of the casting alloy is higher than both the melting point and the desired heat treatment temperature of the infiltration alloy. The casting alloy can be provided in ingot form and melted in the usual manner in the casting technique used by the technician after the restoration has been formed on the die in a manner well-known to one of skill in the art.

The infiltration alloy has similar properties to those described above for the casting alloy, particularly with respect to resistance to oxidation and compatibility with living tissue. In certain embodiments, the infiltration alloy may comprise up to 100% gold, although other embodiments may incorporate other elements; for example, the infiltration alloy may comprise up to 3% of silver to aid in the flow of the infiltration alloy. In certain embodiments, the infiltration alloy may be provided in a powdered form and may be mixed with a liquid carrier for ease of application.

The infiltration alloy is applied to the cast structure, placed in the furnace and brought up to the prescribed temperature so that it diffuses into the surface of the casting alloy. This process creates a layer of bright, oxidation-resistant alloy on the inner and outer surface of the cast structure without affecting the integrity or fit of the original casting. This technique lends itself to most standard techniques used in dentistry today, including but not limited to inlays, full crowns, bridges, ceramic restorations, broken stress bridges, precision attachments or any combination of the above.

In certain embodiments of the present invention, the infiltration alloy is comprised of gold particles which are adapted to diffuse into the cast alloy through a heat treatment process. In certain embodiments, the infiltration alloy thoroughly permeates the surface of the substructure alloy without changing the alloy's integrity, leaving a thin coating of the infiltration alloy on the inner and outer surface of the substructure. A bonding agent may be used in certain embodiments to enhance the bonding of the ceramic layer to the treated substructure. Pure gold has been shown to be effective as a bonding agent. In certain embodiments, the surface of the substructure may be sandblasted with an abrasive such as aluminous oxide to improve adhesion. After creation of the substructure, an external ceramic layer can be created according to conventional techniques.

A second group of embodiments of the present invention comprise methods of forming a dental prosthesis comprising the steps of casting a substructure comprising a casting alloy of a first precious metal and a second precious metal; applying a coating to the surface of the substructure, the coating comprising an infiltration alloy of the first precious metal and a flowing element; and firing the substructure and coating at a temperature sufficient to cause the infiltration alloy to permeate the surface of the substructure.

A third group of embodiments of the present invention comprise methods of forming dental prostheses comprising the steps of: forming an alloy sheet comprising a first precious metal and a second precious metal around a die to form a substructure; soldering the substructure together at the edges; applying an infiltration alloy comprising the first precious metal to a surface of the substructure; and firing the substructure at a temperature sufficient to cause the infiltration alloy to permeate the surface of the substructure The alloys and methods of the present invention are significantly improved over prior alloys and methods. Current practice in the field of the present invention does not incorporate an oxidation resistant, non-toxic alloy in the manner described in the present application. As the material is comprised of alloys of pure elements having a high degree of resistance to oxidation, there is essentially no oxidation of the metal. At the same time, this alloy has sufficient strength to allow construction of bridges. This invention provides a material and technique that is cost efficient and not unduly sensitive to process parameters.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention.

The dental material manufactured according to the present invention is an alloy comprised of a casting alloy and an infiltration alloy, which are combined together through a heat treatment process. It is desirable that both the casting alloy and the infiltrating alloy be resistant to oxidation and compatible with the surrounding living tissue. In one embodiment, gold is the major element of each of the alloys due to its inherent workability, resistance to oxidation, and color, especially when used in combination with ceramics.

In one embodiment, the casting alloy is comprised of only two elements, gold and platinum, with the ratio of platinum to gold in the casting alloy being from 0 to 20% by volume. In one embodiment, the melting temperature of the casting alloy is higher than both the melting point and the desired heat treatment temperature of the second alloy. This alloy can be provided in ingot form and melted in the usual manner in the casting technique used by the technician after the restoration has been formed on the die in a manner well-known to one of skill in the art.

The second or infiltrating alloy has similar properties to those described above for the casting alloy, particularly with respect to resistance to oxidation and compatibility with living tissue. In certain embodiments, the infiltration alloy may comprise up to 100% gold, although other embodiments may incorporate other elements; for example, the alloy may comprise up to 3% of silver to aid in the flow of the infiltration alloy. In addition, the alloy may be provided in a powdered form and may be mixed with a liquid carrier for ease of application.

In one method of manufacture, the infiltrating alloy is applied to the substructure or casting alloy, placed in the furnace and brought up to the prescribed temperature so that infiltrating alloy melts and through capillary action passes around and through the grain structure of the casting alloy. This process results in the deposition of a layer of bright, oxidation resistant alloy on the inner and outer surface of the cast structure without affecting the integrity or fit of the original casting. This technique lends itself to most standard techniques used in dentistry today including but not limited to inlays, full crowns, bridges, ceramic restorations, broken stress bridges, precision attachments or any combination of the above.

Figure 1:
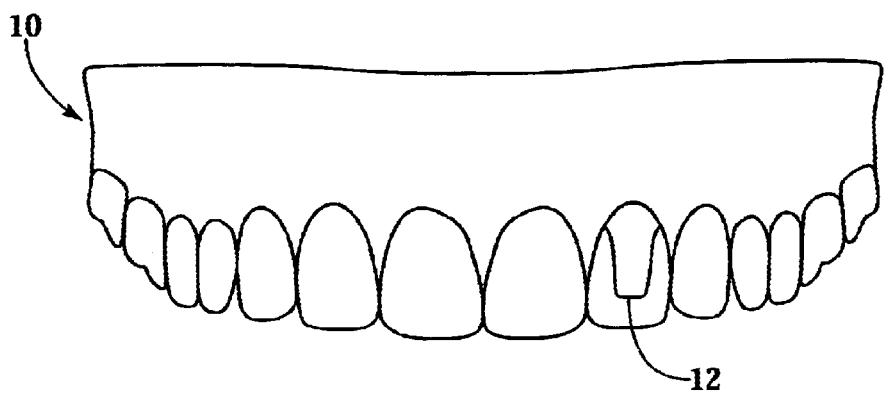
FIG. 1 is a front elevation view of an upper arch with an upper left lateral prepared to receive a crown.

The preparation of a dental crown according to one embodiment of the present invention is shown in FIGS. 1–6. In FIG. 1 there is shown an upper arch 10 with the upper left lateral incisor 12 prepared for a replacement crown. In order to install a dental prosthesis or bridgework to compensate for the loss of the upper left lateral incisor 12, the upper left lateral incisor 12 is cut down by the dentist to a shape that will allow the replacement prosthesis to be placed thereon.

Figure 2:
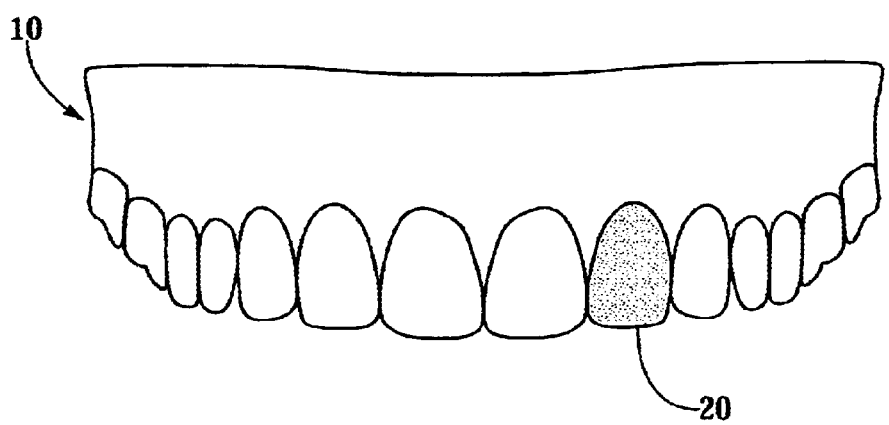
FIG. 2 is a front elevation view of an upper left lateral wax up.

In order to prepare a dental prosthesis according to one embodiment of the present invention, the dentist first prepares an impression of the upper arch 10, from which a die will be made of plaster or a like material in the conventional manner. The die is an accurate model of the patient's teeth and gums. The die will resemble the structure shown in FIG. 1 with the reproduction of the upper left lateral incisor 12. As shown in FIG. 2, a wax pattern is fabricated, using standard crown and bridge principles, over the upper left lateral incisor 12. This is shown in FIG. 2 with the wax substructure 20 formed over the die 12. The wax substructure thus formed is shown in FIG. 3.

Figure 3:
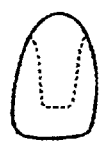
FIG. 3 is an exploded view of an upper left lateral wax up.
Figure 4:
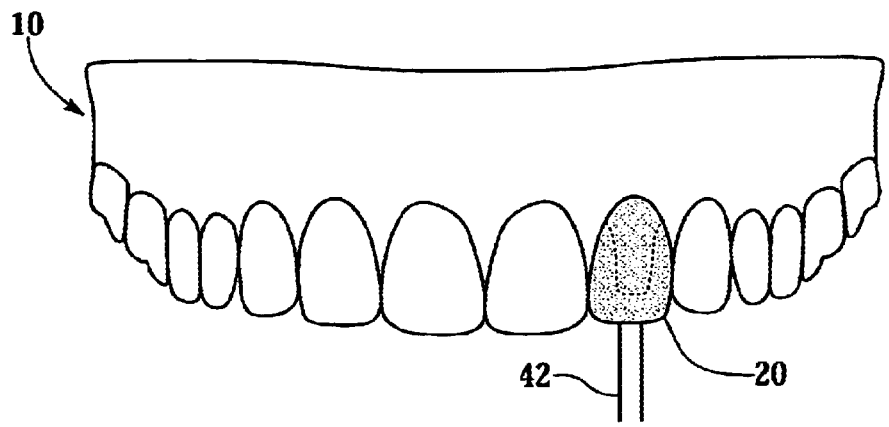
FIG. 4 is a front view of a single wax coping with sprue attached.

The wax substructure pattern shown in FIG. 3 is then invested. This process is begun by attaching sprues to the wax substructure. In the bridge shown in FIG. 4, the sprue 42, which is made of a rigid wax to support the substructure in the investment, is attached to the end of the wax coping 20.

Figure 5:
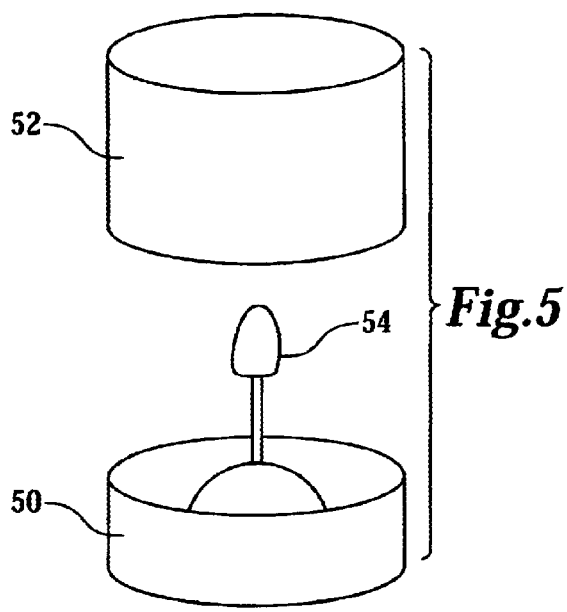
FIG. 5 is a view of a casting ring assembly having a single wax coping with sprue attached.

The sprue 42 with the wax substructure attached is then removed from the die and attached to a rubber sprue former 50 as shown in FIG. 5. A casting ring 52 is placed into the rubber sprue former 50 and sealed to allow a plaster type material to be poured into the top of the ring 52 in a sufficient amount to completely cover and surround the wax substructure 20. After a waiting period, this plaster material will harden and the rubber sprue former 50 may be removed. The plaster material is designed to maintain strength and dimensional stability at a temperature sufficient to eliminate the wax substructure 20 by melting or vaporization. Elimination of the wax substructure 20 from within the plaster form will leave a cavity therein having the shape of the desired crown.

Figure 6:
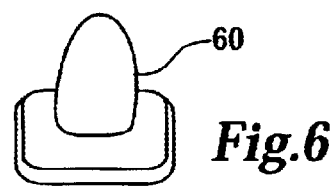
FIG. 6 is an investment casting of a single crown according to one embodiment of the present invention.

In order to make the casting, the ring 52 is removed from the rubber sprue former 50 and is placed into a furnace and heated to a temperature sufficient to melt or vaporize the wax substructure 20. Elimination of the wax substructure 54 from the plaster forms a mold therein. The heated ring 52 is then placed into a centrifugal casting machine and a casting alloy as described above is melted and cast into the mold by centrifugal force. The casting alloy fills the mold forming a substructure exactly like the original wax pattern. A substructure as produced by the above methods is shown in FIG. 6, showing a substructure 60.

After the alloy has cooled, the substructure 60 is cleaned of the plaster investment, the sprue is cut off and the substructure 60 is checked for fit on the dies. The outer surface of the substructure 60 is then finished to a smooth surface. This can be accomplished, for example, through the use of rubber wheels. The crown is filled with the plaster investment material used in the investment and casting process. This is accomplished by either leaving the plaster material in place from prior processing or by taking a small amount of the plaster material and filling the inside of the coping or crown. After the plaster investment has set to a hard consistency, a special infiltration alloy is applied to the surface of the substructure 60. Certain embodiments of the present invention incorporate an infiltration alloy comprising gold and silver. An infiltration alloy comprising 97% gold and 3% silver particles ranging in size between 5 spherical microns and a 60 mesh has been found to be operable for the purposes of the present invention. In one embodiment, the infiltration alloy is applied to the exposed metal in a paste form.

After application of the infiltration alloy to the surface of the substructure 60, the substructure 60 is placed into a furnace and brought up to a temperature corresponding to the fusion point of the infiltration alloy. The infiltration alloy will permeate the substructure 60, leaving a thin coating of the infiltration alloy on the inside and outside surface of the substructure 60. Alternately, infiltration of the substructure can be done using thin foil sheets of the infiltration alloy. In this embodiment, a thin sheet of infiltration alloy, 0.005" in thickness, is cut in a pattern that is adapted around the substructure. The substructure with the infiltrating sheet is then placed in the furnace and the temperature brought up to the fusion point of the infiltrating alloy. In certain embodiments, a sheet of approximately 0.001" is used.

After infiltration, the substructure 60 is cleaned and a thin coat of bonding agent is applied on the outer surface of the substructure 60 to which the ceramic veneer is to be attached. The bonding agent is fired in a furnace to an elevated temperature sufficient to bond the: bonding agent to the substructure 60. In one embodiment, the bonding agent is fired at 1,010 C. After firing, the substructure is ready to have opaque and porcelain processed in the conventional manner. Full inlays or crowns are processed in the same manner as described above except there is no need for the use of the bonding agent. Additionally, it is possible to use preformed crown forms in the same manner as described above if the preformed units are properly modified and adjusted.

Figure 7:
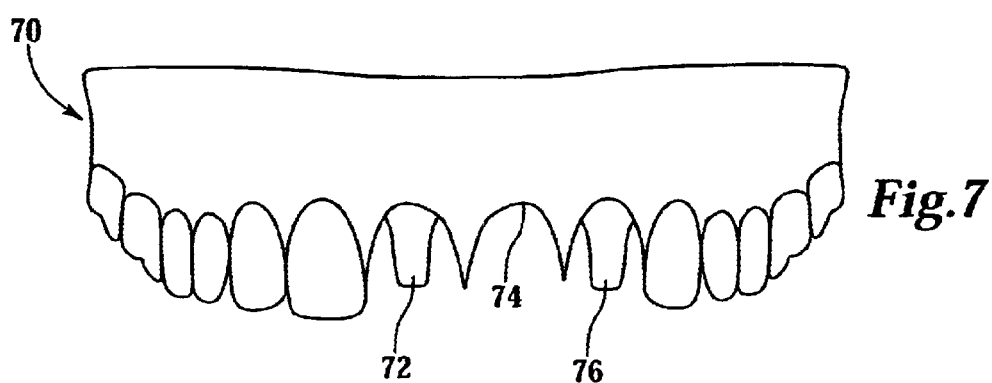
FIG. 7 is a front elevation view of an upper arch with a missing central tooth and having abutment teeth prepared to receive a 3-unit bridge.

The preparation of a dental crown according to a second embodiment of the present invention is shown in FIGS. 7–12. In FIG. 7, there is shown an upper arch 70 with left central incisor 74 missing and right and left abutments 72 and 76 prepared for a bridge. In order to install a dental prosthesis or bridgework to compensate for the loss of the central incisor 74 and the prepared abutment teeth 72 and 76, the abutment teeth 72 and 76 are cut down by the dentist to a shape that will allow the replacement prosthesis to be placed thereon.

Figure 9:
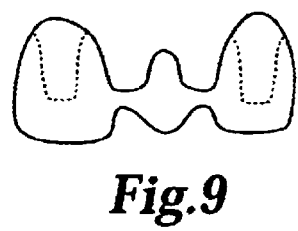
FIG. 9 is an exploded view of three-unit wax up.
Figure 8:
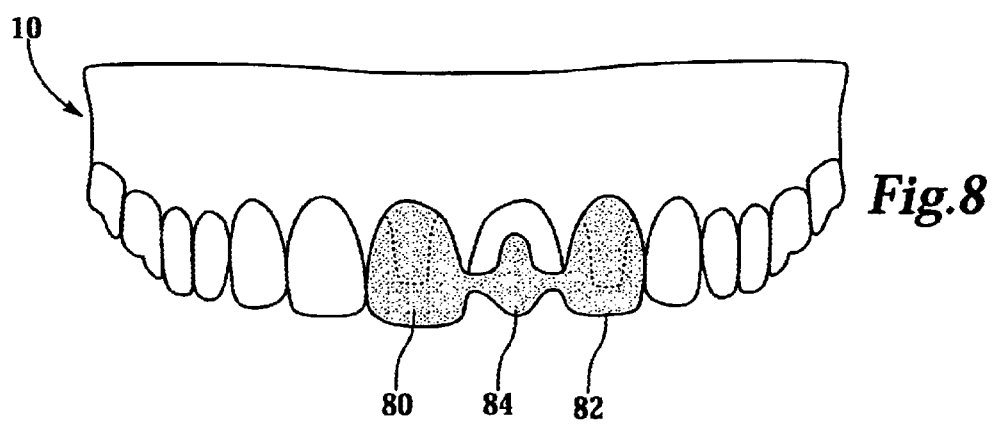
FIG. 8 is a front elevation view of a three-unit wax buildup.
Figure 10:
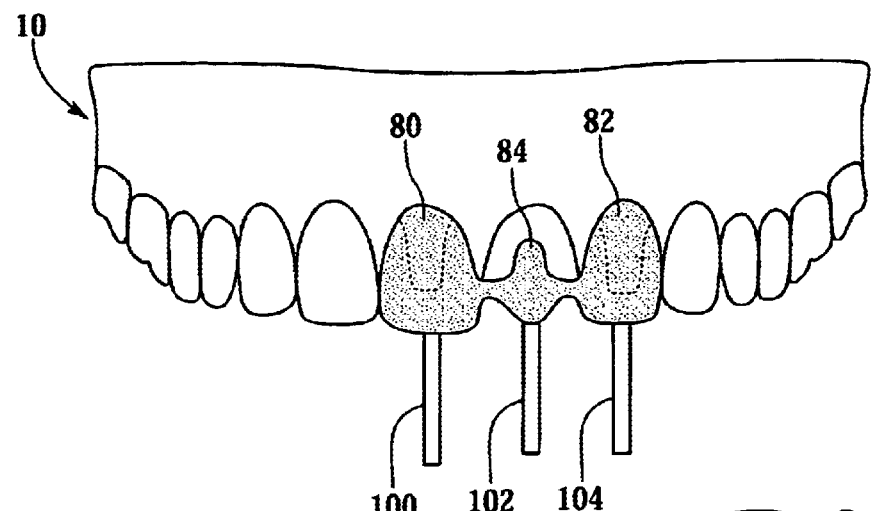
FIG. 10 is a front elevation showing wax substructure of three-unit bridge with sprues attached.
Figure 11:
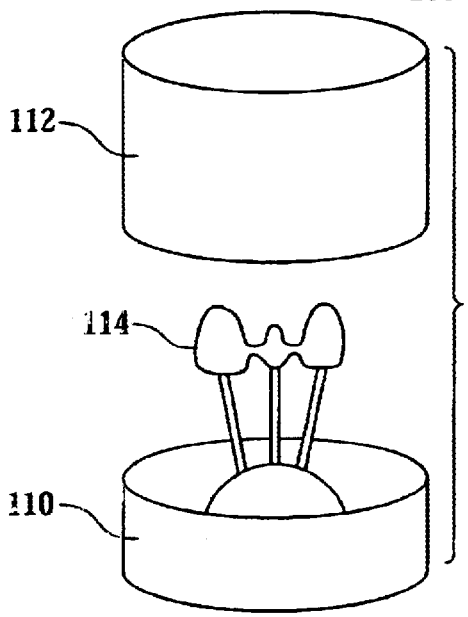
FIG. 11 is a view of a casting ring assembly with three-unit wax superstructure.

In the bridge shown in FIGS. 7, 8, and 9, the construction is according to the usual and conventional techniques. The copings and the pontic area are waxed for adequate strength, proper support and uniform thickness for a veneer, then sprued as shown in FIG. 10 and invested as shown in FIG. 11. The investment is then burned out, cast in one piece, devested, surface prepared and infiltrated in the same manner as a single unit, as described below.

In order to prepare a dental prosthesis for the arch 70 of FIG. 7 according to one embodiment of the present invention, the dentist first prepares an impression of the upper arch 70, from Which a die will be made of plaster or a like material in the conventional manner. The die is an accurate model of the patient's teeth and gums. The die will resemble the structure shown in FIG. 7 with two abutments 72 and 76 for a bridge to replace the missing central 74. As shown in FIG. 8, a wax pattern is fabricated, using standard crown and bridge principles, comprising copings 80 and 82 over the abutments 72 and 76 joined to a wax form known as a pontic 84 placed in the space left by the missing tooth 74. This assembly forms the substructure for the bridge, which is shown in FIG. 9.

The wax substructure pattern shown in FIG. 9 is then invested. This process is begun by attaching sprues to the wax substructure. In the bridge shown in FIG. 10, the sprues 100, 102, and 104, which are made of a rigid wax to support the substructure in the investment, are attached to the end of the wax copings 80 and 82 and the wax pontic 84.

The sprues with the wax substructure 114 attached are then removed from the die and attached to a rubber sprue former 110 as shown in FIG. 11. A casting ring 112 is placed into the rubber sprue former 110 and sealed to allow a plaster type material to be poured into the top of the ring until the wax substructure 114 is completely covered. After a waiting period, this plaster material will harden and the rubber sprue former may be removed. In one embodiment, the waiting period comprises approximately fifteen minutes. The plaster material used for investment is formulated to maintain its strength and dimensional stability at a temperature necessary to eliminate the wax substructure 114 by either melting or vaporization. The elimination of the wax substructure 114 will form a mold inside the plaster.

In order to make the casting, the ring 112 is removed from the rubber sprue former and is placed into a furnace and heated to a temperature sufficient to melt the wax substructure 114. At this temperature the wax substructure 114 melts or vaporizes from within the plaster, forming a mold inside. After evacuation of the wax substructure 114, the heated ring 112 is placed into a centrifugal casting machine and a casting alloy of a special formulation is melted and cast into the mold by centrifugal force. The casting alloy then fills the mold forming a substructure having a shape substantially identical to the original wax substructure 114.

Figure 12:
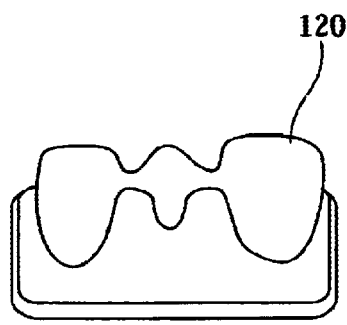
FIG. 12 is a cast substructure as produced by the methods shown in FIGS. 7–11.

A cast substructure as produced by the above methods is shown in FIG. 12, showing a substructure 120. After the substructure 120 has cooled, the substructure 120 is cleaned of the plaster investment, the sprues are cut off, and the substructure 120 is checked for fit on the dies. In certain embodiments, the outer surface of the substructure 120 may be finished to a smooth surface through the use of rubber wheels or other apparatus. After this mechanical processing, the interior portions of the substructure 120 are filled with the plaster investment material used in the investment and casting process. This is accomplished by either leaving the plaster material in place inside the coping or crown or by taking a small amount of the plaster material and filling the inside of the coping or crown. After the plaster investment material has set to a hard consistency, an infiltration alloy is applied to the exposed metal of the substructure 120.

In certain embodiments, the infiltration alloy comprises an alloy of gold and silver. An alloy of 97% gold and 3% silver has been found to be operable for the purposes of the present invention. In one embodiment, the infiltration alloy is provided in a thin paste form to be painted over the exposed metal of the substructure 120. Alternately, infiltration of the substructure 120 can be done using thin foil sheets of the infiltration alloy. In this embodiment, a thin sheet of infiltration alloy is cut to size and bent over the substructure 120. In one embodiment, a sheet of approximately 0.001" is used.

After application of the infiltration alloy to the, substructure 120, the assembly is placed into a furnace and brought up to an elevated temperature. In one embodiment, this temperature correlates to the fusion point of the infiltration alloy. At the elevated temperature, the infiltration alloy permeates into the substructure alloy, leaving a thin coating of the infiltration alloy on the inside and outside surface of the substructure 120.

After processing in the furnace, the plaster investment is removed from the substructure and cleaned. In certain embodiments, a thin coat of bonding agent may be applied on the outer surface to which the ceramic veneer is to be attached. The bonding agent may comprise, for example, pure gold. The bonding agent is fired in a furnace at an elevated temperature sufficient to bond the agent to the substructure 120. For a bonding agent comprising pure gold, a temperature of 1,010 C. has been found to be operable. After firing the substructure 120, opaque and porcelain can be processed in the conventional manner. Full metal inlays, crowns or bridges are processed in this same manner as described above except there is no need for the use of the bonding agent.

An alternative method of constructing a coping would be to process the coping from a sheet of gold alloy of the same formula as previously described. The gold sheet is cut to a pattern that is then adapted around the die of the prepared tooth. The seams are soldered together and the coping is infiltrated in the same manner as described above in connection with the cast coping.

It is also possible to use a preformed coping made of the same gold alloy material in sheet form. In this application, a preformed coping close to the size of the prepared tooth is placed on the die and swedged to shape. The margins are then trimmed and the surface finished and infiltrated as described above.

Figure 13:
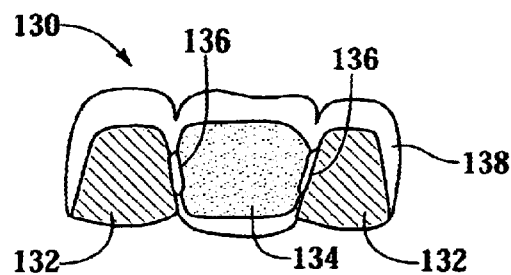
FIG. 13 is a bridge constructed according to traditional sintering methods.
Figure 14:
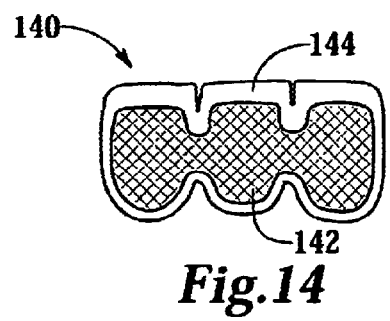
FIG. 14 is a complete bridge constructed according to the present invention.

A bridge 130 constructed according to a sintering technique, as shown in FIG. 13, is completely different from any of the various embodiments of the process described above. The abutment copings 132 are fabricated according to traditional sintering techniques. The pontic 134 for the bridge 130 is then waxed, cast, and then wedged between the sintered abutment copings 132 so that the pontic 134 is supported by the copings 132 and abutment teeth. The bridge 130, assembled on the model and dies, is drawn off the model, invested, and soldered together at joints 136. The bridge 130 is then capped with a porcelain veneer 138. Unlike the process described above and shown in FIGS. 7–12, resulting in a bridge 140 shown in FIG. 14, the sintering process makes use of a pontic 134 and copings 132 made of different materials. The entire substructure 142 of bridge 140 is cast of one alloy in one piece and capped with a porcelain veneer 144.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method of forming a dental prosthesis comprising:
   casting a substructure comprising a casting alloy of a first precious metal and a second precious metal;
   applying a foil to the surface of the substructure, the foil comprising an infiltration alloy comprising the first precious metal and a flowing element and having a thin coating of silver or silver chloride applied to one surface; and
   firing the substructure and coating at a temperature sufficient to cause the infiltration alloy to permeate the surface of the substructure.

2. The method of claim 1 wherein the first precious metal comprises 80–99.5% of the casting alloy by volume and the second precious metal comprises 0.5–20% of the casting alloy by volume.

3. The method of claim 1 wherein the first precious metal comprises 97–99.5% of the foil by volume and the flowing element comprises 0.5–3% of the foil by volume.

4. The method of claim 1 wherein the foil comprises 99.5% gold.

5. The method of claim 1 wherein the foil has a thickness of approximately 0.001 inches.

6. A method of forming a dental prosthesis comprising:
   forming a uniform alloy sheet comprising an infiltration alloy comprising gold and platinum around a die to form a substructure;
   soldering the substructure together at the edges;
   applying a foil comprising gold to a surface of the substructure; and
   firing the substructure at a temperature sufficient to cause the infiltration alloy to permeate the surface of the substructure.

7. The method of claim 6 wherein the alloy sheet is approximately 0.2 mm in thickness.

8. The method of claim 6 further comprising the step of cutting the alloy sheet to shape.

9. The method of claim 6 wherein the alloy sheet is preformed into one of a number of various shapes and sizes suitable for forming.

* * * * *